US00PP36957P2

(12) United States Plant Patent
Ruter

(10) Patent No.: US PP36,957 P2
(45) Date of Patent: Sep. 16, 2025

(54) ***THUJA* PLANT NAMED 'RutThu7'**

(50) Latin Name: *Thuja occidentalis*
Varietal Denomination: RutThu7

(71) Applicant: University of Georgia Research Foundation, Inc., Athens, GA (US)

(72) Inventor: John M. Ruter, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 19/016,915

(22) Filed: Jan. 10, 2025

(51) Int. Cl.
*A01H 7/00* (2006.01)

(52) U.S. Cl.
USPC ..... Plt./213

(58) Field of Classification Search
USPC ..... Plt./213
CPC ..... A01H 7/00; A01H 5/12; A01H 5/00
See application file for complete search history.

(56) References Cited

U.S. PATENT DOCUMENTS

PP35,180 P3 * 5/2023 Ruter ..... A01H 7/00
Plt./213

* cited by examiner

*Primary Examiner* — June Hwu
(74) *Attorney, Agent, or Firm* — Meunier Carlin & Curfman LLC

(57) ABSTRACT

A new and distinct cultivar of *Thuja* plant named 'RutThu7', characterized by its nice columnar form, dark green foliage that does not have chartreuse tips and lack of stem canker and root rot issues can be grown in USDA Zone 8a and is well suited for small urban gardens.

2 Drawing Sheets

Figure 1:
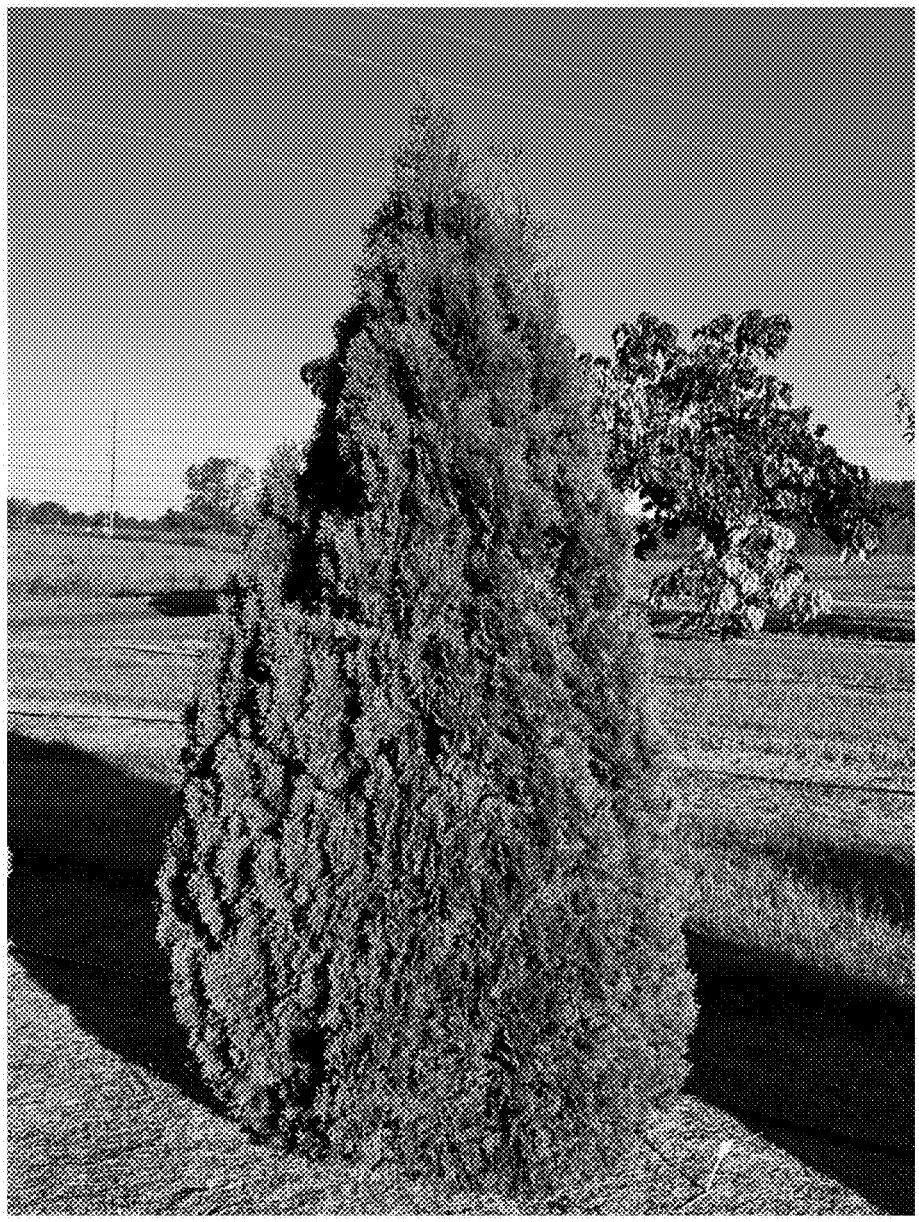

Botanical Designation: *Thuja occidentalis.*
Variety Denomination: 'RutThu7'.

BACKGROUND

The present invention relates to a new and distinct cultivar of *Thuja*, botanically known as *Thuja occidentalis* and hereinafter referred to by the variety name 'RutThu7'.

The new *Thuja* cultivar 'RutThu7' is a product of open pollination of *Thuja occidentalis* 'Pyramidalis' (unpatented). The open-pollinated seeds were obtained in 2014 from Estonia. Seedlings were planted in Watkinsville in 2015. The new cultivar 'RutThu7' was selected for its upright, oval, columnar growth form, darker green color than *Thuja occidentalis* 'Emerald Green' (unpatented).

Asexual reproduction of the new *Thuja* 'RutThu7' using hardwood cuttings has been continued in Watkinsville, GA since 2019. Observations of the resulting progeny have shown that the unique features of this new Thuja 'RutThu7' are stable and reproduced true to type in successive generations.

SUMMARY OF THE INVENTION

The new *Thuja* cultivar 'RutThu7' has not been observed under all possible environmental conditions. The phenotypes may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new Thuja cultivar named 'RutThu7'. These characteristics in combination distinguish 'RutThu7' as a new and distinct *Thuja* cultivar:

1. Upright, oval, columnar growth form.
2. Slower growth rate than *Thuja occidentalis* 'RutThu5' (U.S. Plant Pat. No. 35,180).
3. Compatibility with smaller, urban gardens.
4. Lack of stem cankers or root rot issues compared to 'Emerald Green'.

Plants of the 'RutThu7' can be compared to a similar cultivar *Thuja occidentalis* 'RutThu5' in that the height to width ratio of 'RutThu7' is 2.0 which is equal to that of 'RutThu5'. 'RutThu7' has a similar columnar shape as 'RutThu5' while being smaller (both shorter and narrower) than 'RutThu5' (which is about 123" ×62" compared to about 98" ×48" for 'RutThu7'). The new *Thuja* 'RutThu7' also differs from 'RutThu5' in that 'RutThu7' exhibits a slower growth rate over a 9-year period. 'RutThu7' may also be compared to the cultivar *Thuja occidentalis* 'American Pillar' (U.S. Plant Pat. No. 20,209). 'RutThu7' has a slower growth rate and is shorter (about 98" compared to about 20-30' for 'American Pillar') than 'American Pillar'.

The new *Thuja* 'RutThu7' differs from the female parent plant in that the female 'Pyramidalis' is reported to grow 20-30' tall, while the new *Thuja* 'RutThu7' grows about 98" tall. 'RutThu7' may also be compared to the cultivar *Thuja occidentalis* 'Emerald Green'. 'RutThu7' has a more columnar form than 'Emerald Green'. The foliage of 'RutThu7' is darker green and does not have the chartreuse new growth of 'Emerald Green'. Lastly, 'RutThu7' lacks the stem canker and root rot issues commonly observed with 'Emerald Green'.

BRIEF DESCRIPTION OF THE PHOTOGRAPHS

The accompanying, colored photographic illustrations show the overall appearance and distinct characteristics of the new cultivar *Thuja* 'RutThu7' showing the colors as true as possible. Colors in the photographs may differ slightly from the color values cited in the detailed botanical description. The photographs were taken around October 2024 of plants grown outdoors in Watkinsville, Georgia.

The photograph labeled FIG. 1 depicts a side view of a typical 9-year-old 'RutThu7' plant showing the upright, columnar form and features.

Figure 2:
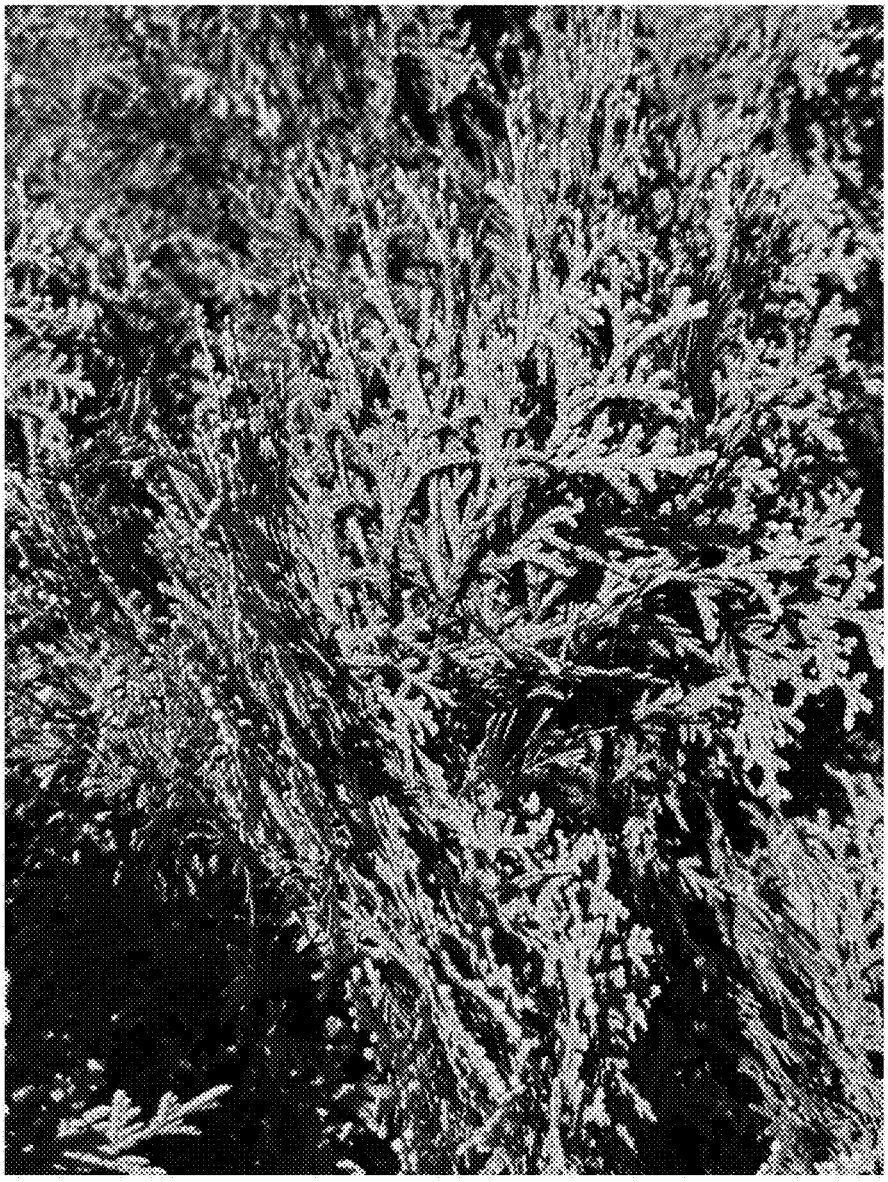

The photograph labeled FIG. 2 depicts a close-up view of the branches and needles of a typical 9-year-old 'RutThu7' plant showing the dark green color and lack of chartreuse-coloring on new growth.

DETAILED BOTANICAL DESCRIPTION

The following traits have been consistently observed in the original plants of the new varieties and in asexually propagated progeny grown in Watkinsville, Georgia, and, to the best knowledge of the inventors, their combination forms the unique characteristics of the new variety 'RutThu7'.

The aforementioned photographs and following observations, measurements, and values describe plants of the *Thuja* cultivar named 'RutThu7'. Data were collected from a horticulture farm in Watkinsville, Georgia from 9-year-old plants. The average low temperatures ranged from about 20° F. to 30° F. in the winter and about 90° F. to 100° F. in summer. General light conditions are normal sunlight and numerical values represent averages of typical plant types. The data were collected in December 2023 and August 2024.

Throughout this specification, color names beginning with a small letter signify that the name of that color, as used in common speech, is aptly descriptive. Color names beginning with a capital letter designate values based upon the R.H.S. Colour Chart, 5th edition published by the Royal Horticultural Society, London, England in 2007, except where general terms of ordinary dictionary significance are used.

Botanical Classification: *Thuja* 'RutThu7'.

Commercial Classification: Ornamental conifer.

Parentage: Open pollination of *Thuja occidentalis* 'Pyramidalis' by unknown pollen parents.

Growth and Propagation:

- *Propagation type*.—Terminal or sub-terminal hardwood cuttings.
- *Growth rate*.—Slow to moderate.
- *Average growth rate per year*.—25-28 cm height increase per year.

*Root description*.—Typically about 2-6 roots arising from the base of the cuttings.

*Rooting habit*.—Good.

Plant description:

- *Habit*.—Upright conical, columnar.
- *Usage*.—Various uses, including landscaping, ornamental, container, border, hedge, urban gardening, and mass planting.
- *Vigor*.—Good.
- *Size*.—Height: From soil level to top of plant is about 98 inches. Width: About 48 inches. Ratio of height to width: About 2.0.
- *Average trunk diameter*.—3.0 cm diameter at 1.4 m height.
- *Bark surface texture*.—Coarse and flaking.
- *Bark color designation* (*RHS*).—Greyed-orange 177A.
- *Winter foliage color* (*RHS*).—Greyed-orange 165C.

Branch/Stem (terminal tuft):

- *Quantity*.—5 branchlets per linear foot.
- *Length*.—About 3-7 cm.
- *Base Diameter* (*of* 2 *year stem*).—About 3-4 mm at 15 cm from tip.
- *Branch angle*.—Variable, but on average about 65° from horizontal.
- *Odor* (*of bruised stem*).—Mild evergreen scent.
- *Internode length*.—About 5-20 mm (about 5 internodes per lateral branch).
- *Color* (*RHS*) (*at* 0.5 *year*).—Yellow Green 144A to greyed-orange 172B.
- *Color* (*RHS*) (*new growth*).—Dark green 137D.
- *Strength of lateral branches*.—Good.
- *Pubescence*.—None.
- *Shape*.—Round.

Leaf:

- *Leaf type*.—Scale.
- *Mature size* (*L* × *W*).—About 2 mm × about 3 mm.
- *Arrangement on stem*.—Decussate.
- *Aspect*.—Upright to slightly spreading.
- *Color* (*RHS*).—Upper: Green 138A. Lower: Green 138A.
- *Apex*.—Acute-attenuate.
- *Base*.—Rounded.
- *Margin*.—Smooth/hyaline.
- *Shape*.—Flattened, decussate no lobes present.
- *Pubescence*.—None.
- *Venation*.—None.
- *Texture*.—Waxy, abaxial gland present.
- *Odor when crushed*.—Mild evergreen.

Long Shoots:

- *Facial Gland*.—Present.
- *Leaf Shape*.—Linear.
- *Color*.—Green 138A.
- *Tips*.—Free/acuminate.
- *Apex*.—Acute-attenuate.
- *Coning production*.—None.
- *Seed*.—None.

Weather/temperature tolerance: Plants of the new *Thuja* have been observed to grow in USDA Zone 8a, with cold hardiness, and *Thuja* have a typical USDA Zone range of 3-8. Plants of the new *Thuja* have also been observed to be resistant to stem dieback (i.e., *Pestalotiopsis* sp., *Seridium cardinale*) under hot, dry conditions.

Disease/pest resistance: To date, plants of the new *Thuja* have been observed to have disease resistance (i.e., *Phytophthora* sp.) in USDA Zone 8a when grown under standard conditions.

What is claimed is:

1. A new and distinct cultivar of *Thuja* plant named 'RutThu7' as illustrated and described herein.

* * * * *